US00PP19655P2

(12) United States Plant Patent
Tam

(10) Patent No.: US PP19,655 P2
(45) Date of Patent: Jan. 20, 2009

(54) ***WISTERIA* PLANT NAMED 'BETTY TAM'**

(50) Latin Name: *Wisteria floribunda*
Varietal Denomination: Betty Tam

(75) Inventor: Patrick Tam, Tulsa, OK (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 11/894,995

(22) Filed: Aug. 22, 2007

(51) Int. Cl.
*A01H 5/00* (2006.01)

(52) U.S. Cl. ..... Plt./226
(58) Field of Classification Search ..... Plt./226
See application file for complete search history.

*Primary Examiner*—Wendy C. Haas
(74) *Attorney, Agent, or Firm*—Penny J. Aguirre

(57) ABSTRACT

A new cultivar of *Wisteria floribunda* named 'Betty Tam', characterized by its repeat blooming habit, its large panicles of blue-violet flowers, its cold hardiness to U.S.D.A. Zone 5 and its vigorous growth rate and ease of propagation.

2 Drawing Sheets

Botanical classification: *Wisteria floribunda.*
Cultivar designation: 'Betty Tam'.

BACKGROUND OF THE INVENTION

The present invention relates to a new and distinct cultivar of *Wisteria* plant, botanically known as *Wisteria floribunda* 'Betty Tam' and will be referred to hereafter by its cultivar name, 'Betty Tam'. The new cultivar represents a new Japanese wisteria grown as a vine or shrub for landscape use.

'Betty Tam' was discovered by the inventor in Claremore, Okla. in 1950 as a whole plant mutation derived from seed sown from unnamed plants of *Wisteria floribunda.* The new cultivar was observed over a period of 40 years and subsequently grafted onto understock for further evaluation.

Asexual reproduction of the new cultivar was first accomplished by grafting in Tulsa, Okla., by the inventor in 1996. Asexual reproduction by grafting and stem cuttings has determined that the characteristics of this cultivar to be stable and reproduced true to type in successive generations.

SUMMARY OF THE INVENTION

The following traits have been repeatedly observed and represent the characteristics of the new cultivar as observed for over forty years in Oklahoma. These attributes in combination distinguish 'Betty Tam' from other varieties of *Wisteria* known to the inventor.

1. 'Betty Tam' exhibits the ability to repeat bloom during the growing season, initially blooming for 2 to 3 weeks in spring and repeating bloom 2 to 3 times throughout the season.
2. 'Betty Tam' exhibits large panicles of lavender flowers.
3. 'Betty Tam' is hardy to U.S.D. S. Zone 5.
4. 'Betty Tam' has a vigorous growth habit and is readily propagated by grafting and stem cuttings.

'Betty Tam' differs from the parent species, *Wisteria floribunda,* in having a repeat blooming habit whereas the species blooms only in spring. The closest comparison plants to; 'Betty Tam' known to the inventor are *Wisteria floribunda* 'Longissima' and *Wisteria frutescens* 'Amesthyst Falls' (both unpatented). 'Betty Tam' is similar to 'Longissima' in having a similar flower color, however 'Longissima' has longer flower panicles and lacks a repeat blooming habit. 'Amethyst Falls' is similar to 'Betty Tam' in having a repeat blooming habit, however, 'Amethyst Falls' has smaller, rounder inflorescences and is a cultivar of *Wisteria frutescens.*

BRIEF DESCRIPTION OF THE DRAWING

The accompanying colored photographs illustrate the overall appearance and distinct characteristics of the new *Wisteria.* The photographs were taken of plants and plant parts of a plant approximately 10 years in age as grown outdoors in a trial bed in Oklahoma.

The photograph in FIG. 1 is a view of a plant of 'Betty Tam' in bloom and illustrates its plant habit.

Figure 1:
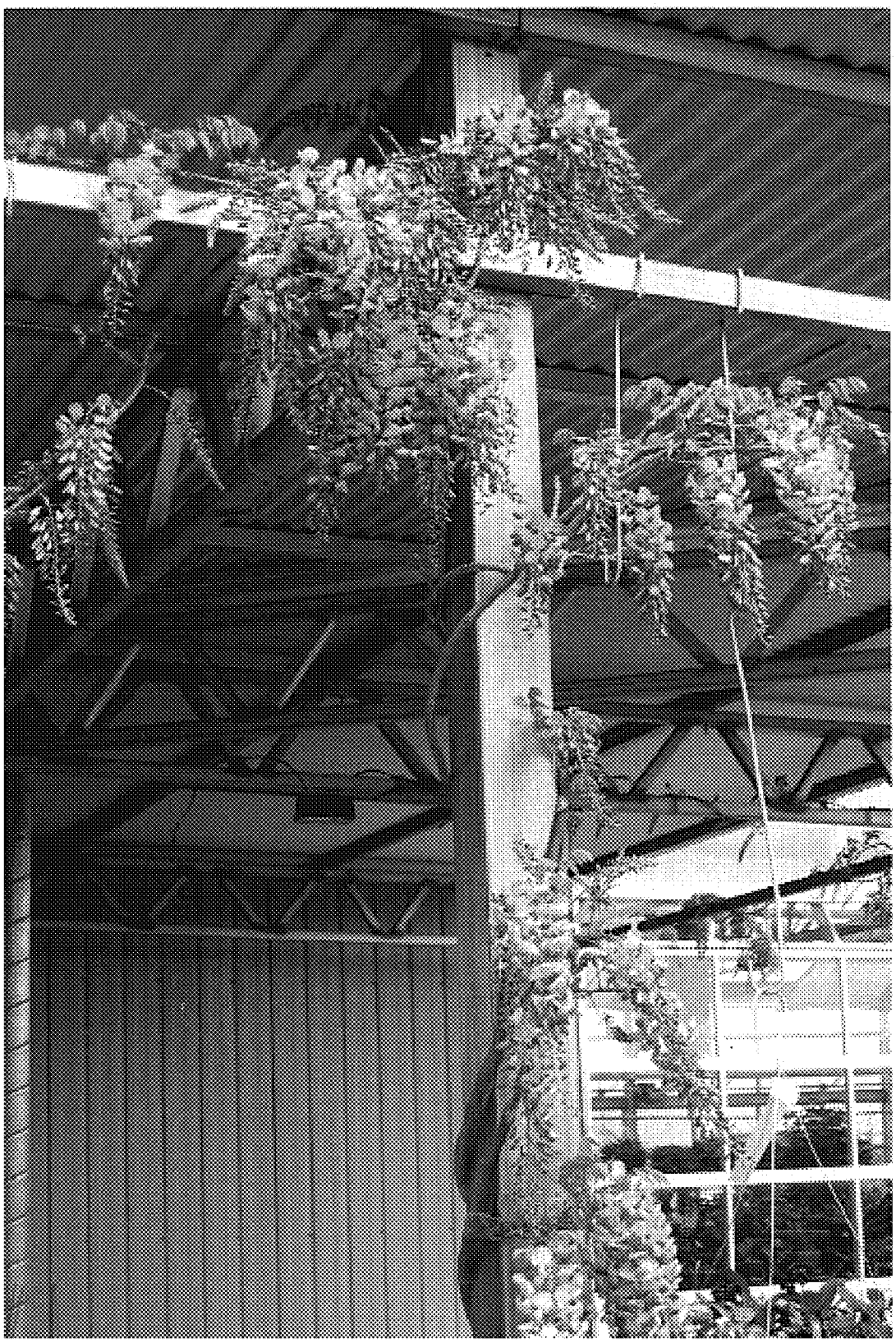
Figure 2:
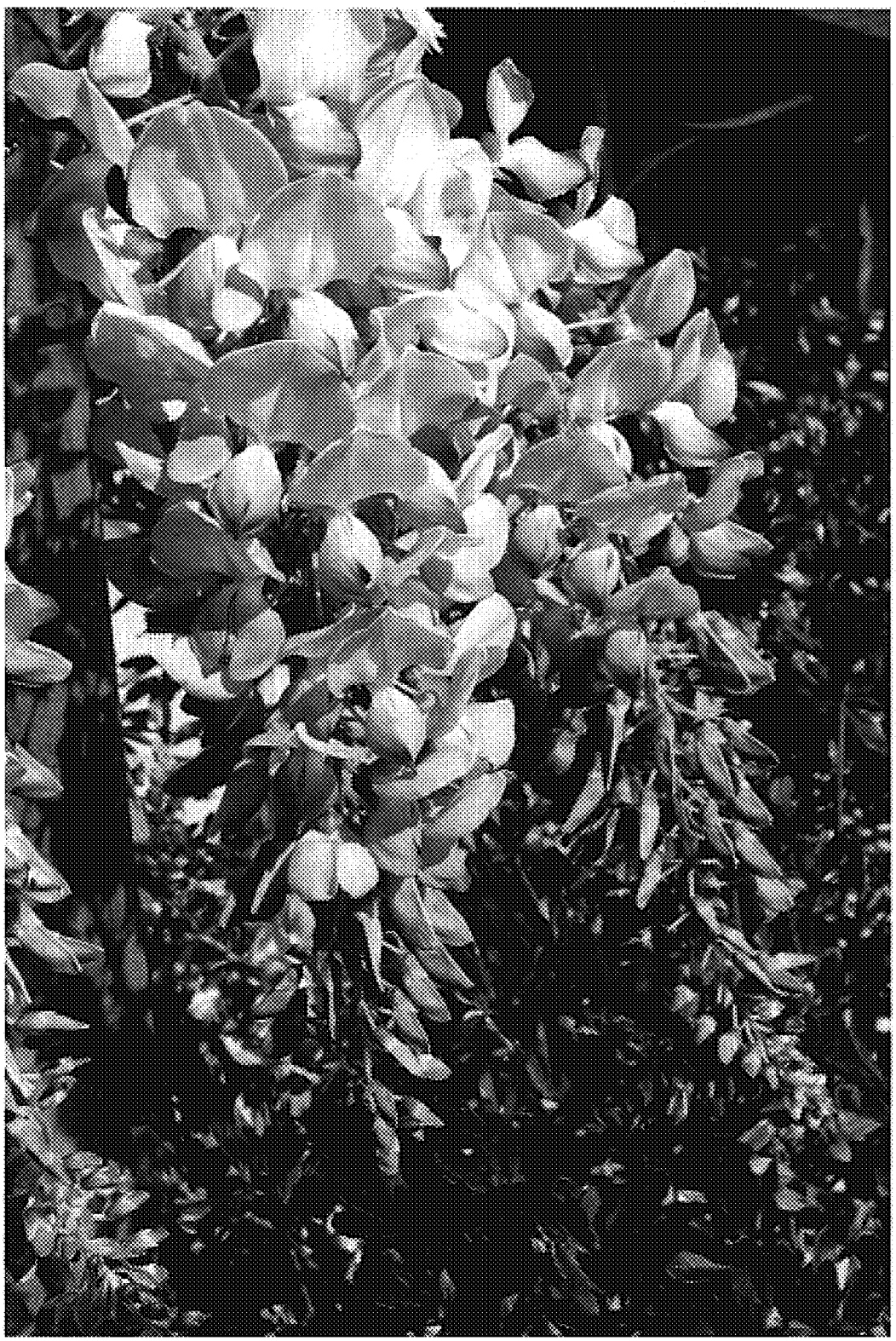

The photograph in FIG. 2 is of a close-up view of the flowers of 'Betty Tam'.

The colors in the photographs are as close as possible with the photographic and printing technology utilized. The color values cited in the detailed botanical description accurately describe the colors of the new *Wisteria.*

DETAILED BOTANICAL DESCRIPTION OF THE PLANT

The following is a detailed description of 6 year-old plants of the new cultivar as grown outdoors in 15 gallon containers in Park hill, Okla. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

Botanical classification: 'Betty Tam' is a cultivar of *Wisteria floribunda.*

General description:

*Blooming period.*—2 to 3 weeks in spring and repeating 2 to 3 times during the growing season.

*Plant type.*—Deciduous woody vine.

*Plant habit.*—Climbing vine or weeping shrub if pruned.

*Height.*—Vines reach about 9 M (30 feet).

*Cold hardiness.*—U.S.D.A. Zone 5.

*Diseases and pests.*—No susceptibility or resistance to diseases or pests has been observed.

*Root description.*—Coarse.

Growth and Propagation:

*Propagation.*—Stem cuttings or grafting.

Rooting. —Roots initiate in 10 to 14 days grown under greenhouse conditions at an average temperature of 20° C. without supplemental light or bottom heat.

*Growth rate.*—Vigorous.

Stem description:

*Branch habit.*—Freely branched in irregular pattern.

*Stem diameter.*—Young stems average 4 mm, mature secondary branches average 2 cm.

*Stem shape.*—Oval when young, becoming round when woody, contorted due to irregular branching and vining.

*Stem color.*—Young stems 144A, mature bark 199C with areas of 200A showing through and lenticels 162D.

*Stem surface.*—Gabrous when young, smooth but bark-like when mature.

*Stem internode length.*—Variable; ranging from whorls to 17 cm.

Foliage description:

*Leaves.*—Oblanceolate in overall outline, division is odd pinnate; typically 5 pairs of opposite and a terminal leaflet, arrangement is initially in whorls becoming alternate, average internode length 7 cm, average of 28 cm in length and 17 cm in width when mature, about 8 per stem 40 cm in length.

*Leaflets.*—Oval to ovate in shape, cuneate to rounded base, acuminate apex, venation; pinnate pattern, conspicuous but not prominent, mid rib 144B with others matching leaf color, recessed on upper surface and raised on lower surface, entire margins, petiolate attachment, opposite arrangement, surface; glabrous on upper surface and glabrous and semi-glossy on lower surface, color when expanding on upper and lower surface; 144A, color when mature; upper surface 137A and lower surface 137B, size; up to about 9 cm in length, up to about 4.7 cm in width.

*Petioles.*—Average of 3 mm in length and 1.5 mm in width (swollen at attachment), 144A in color, surface is glabrous.

*Rachis.*—Average on 20 cm in length and 1.5 mm in width on mature leaves, 144A in color, surface is glabrous.

*Stipules.*—Not present.

Flower Description:

*Inflorescence.*—Terminal and auxiliary racemes of pea-like flowers, blooms from the base to the apex, cascading.

*Inflorescence size.*—Up to 28 cm in length and 8 cm in width.

*Lastingness of inflorescence.*—2 to 3 weeks.

*Flower size.*—About 2 cm in depth and about 1.8 cm in diameter.

*Flower fragrance.*—Hyacinth-like.

*Flower number.*—About 40 per inflorescence.

*Peduncle.*—Oval in shape, up to 28 cm in length and ranges from 3 mm in width at the base of the inflorescence to 1 mm in width at the apex, 144A to 144B in color, pubescent surface with some nodules, flowers are arranged irregularly (both apposite and alternate), internode length is an average of 3.5 mm.

*Petiole.*—Average of 1.8 cm in length and 1 mm in width, oval in shape, 85 in color with a tinge on underlying green, puberelent surface.

*Flower buds.*—Kidney shaped, about 1.9 cm in length and 9 mm in width prior to opening, color emerges N89B to N89C to 86B changing to N82A blended with N82B with an apex of N89C and calyx portion of 83C to 83D prior to opening.

*Flower type.*—Papilionaceous, held nearly horizontal to stem.

*Calyx.*—Campanulate, about 6 mm in length and 6 mm in diameter, surface is pubescent, 83C to 83D in color, sepals; 5, fused with the exception of apex of, free portion is triangular in shape 2 mm in width and 2 mm in depth with an acute apex.

*Corolla features.*—Papilionaceous (4 segments) with a keel, an inner lip and 2 lateral wings, inner lip; comprised of two lobes that are folded around stamens and pistil, lobes are reniform in shape, about 1.5 cm in length and 8 mm in width, N88C to N88D in color with upper half overlaid with 86A and 86B, base 155C, rounded fused apex, lateral wings; loosely surround inner lip, oblong-reniform in shape, about 1.8 cm in length and 9 mm in width, upper and lower surface is N82B to N82C in color with a lower ⅔ 92B to 92D and tip of apex N89C, rounded apex, keel; reflexed, orbicular in shape with cordate apex, 1.8 cm in length and 2 cm in width, upper surface and lower surface are N88C to 88D in color with overlay of N88B, apex N89C, and base on center region of 155C, all segments; glabrous in texture, entire margin, base is rounded on keel and the base of other segments has a short attenuated and oblique section about 3 mm in length, 1 mm in width, and 155C in color, flower fade to a bi-color blend of 160A and N88A and drop as seed pod develops.

*Receptacle.*—Disk-shaped, gelatinous, 145C in color, about 2 mm in diameter and 1.2 mm in depth.

Reproductive organs:

*Gynoecium.*—Pistil, about 1.4 cm in length, 1 mm in width; style is horizontal to ovary, 0.3 mm in width, 8 mm in length and 144D in color; stigma minute, too small to color read; Ovary is superior, hairy surface, 144B in color, 9 mm in length and 1 mm in width; stipe is 144D in color, 2 mm in length and 1 mm in width.

*Androcoecium.*—10 stamens, coherent; filament is 1.8 cm in length, <1 mm in width and 155C in color; anther is dorsifixed, 0.5 mm in length, 0.3 mm in width and 160A in color, pollen is not visually apparent.

*Fruit and seed.*—Fruit; a loment legume, elongated, 2-valved, up to 12 cm in length and 1.6 cm in width, velutinous, color is 146A covered with fine hairs 150D, seed; round but flattened, average of 9 mm in diameter and 4 mm in depth, average of 5 per pod, between 144C and 144D in color.

I claim:

1. A new and distinct cultivar of *Wisteria* plant named 'Betty Tam' as herein illustrated and described.

* * * * *